United States Patent
Waterson et al.

(10) Patent No.: US 8,129,412 B2
(45) Date of Patent: Mar. 6, 2012

(54) HYDANTOIN DERIVATIVES USEFUL AS METALLOPROTEINASE INHIBITORS

(75) Inventors: David Waterson, Cheshire (GB); David Jonas Persson, Perstorp (SE)

(73) Assignee: AstraZeneca AB, Södertälje (SE)

( * ) Notice: Subject to any disclaimer, the term of this patent is extended or adjusted under 35 U.S.C. 154(b) by 1029 days.

(21) Appl. No.: 11/793,358

(22) PCT Filed: Dec. 14, 2005

(86) PCT No.: PCT/GB2005/004811
§ 371 (c)(1),
(2), (4) Date: Feb. 19, 2008

(87) PCT Pub. No.: WO2006/064218
PCT Pub. Date: Jun. 22, 2006

(65) Prior Publication Data
US 2008/0280950 A1     Nov. 13, 2008

(30) Foreign Application Priority Data
Dec. 15, 2004   (GB) .................... 0427403.1

(51) Int. Cl.
*A61K 31/445*     (2006.01)
*C07D 401/12*     (2006.01)

(52) U.S. Cl. ...................... 514/326; 546/210

(58) Field of Classification Search .......... 514/326; 546/210
See application file for complete search history.

(56) References Cited

U.S. PATENT DOCUMENTS

| | | | |
|---|---|---|---|
| 6,734,183 B2 | 5/2004 | Barlaam et al. | |
| 6,734,184 B1 | 5/2004 | Barlaam et al. | |
| 6,916,817 B1 | 7/2005 | Tucker | |
| 7,122,551 B2 | 10/2006 | Barlaam et al. | |
| 7,427,631 B2 * | 9/2008 | Eriksson et al. | 514/318 |
| 7,485,644 B2 * | 2/2009 | Finlay et al. | 514/252.14 |
| 2004/0127528 A1 | 7/2004 | Eriksson et al. | |
| 2004/0171641 A1 | 9/2004 | Barlaam et al. | |
| 2006/0287338 A1 | 12/2006 | Barlaam et al. | |
| 2007/0197542 A1 | 8/2007 | Finlay et al. | |

FOREIGN PATENT DOCUMENTS

| | | |
|---|---|---|
| WO | WO 0012478 | 3/2000 |
| WO | WO 0075108 | 12/2000 |
| WO | WO 0162742 | 8/2001 |
| WO | WO 02/074767 | 9/2002 |
| WO | WO 2005/000822 | 1/2005 |

OTHER PUBLICATIONS

Wikipedia "Matrix metalloproteinase" p. 1-8, from internet (2011).*
.Kim et al. "Structure-based design of potent and selective inhibitors of collagenase-3 (MMP-13)"., Bioorganic & medicinal chemistry letters, vol. 15, No. 4, pp. 1101-1106 (2005).*
Savi et al. "The desitn and synthesis . . . " Bioorg. Med. Chem. Letts v.21, pp. 1376-1381 (2011).*

* cited by examiner

*Primary Examiner* — Celia Chang
(74) *Attorney, Agent, or Firm* — Connoll Bove Lodge & Hutz LLP

(57) ABSTRACT

Formula (I) wherein $R^1$ is a (2-4C)alkyl and is substituted by two or more fluorine groups and $R^2$ is methyl or ethyl, or a pharmaceutically acceptable salt thereof; processes for their preparation, pharmaceutical compositions containing them and their use in the treatment of diseases or medical conditions mediated by metalloproteinase enzymes.

(I)

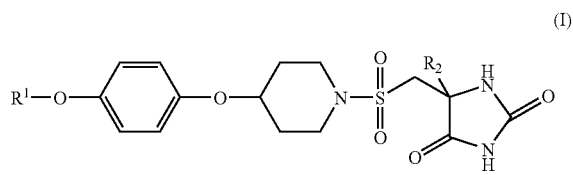

8 Claims, No Drawings

HYDANTOIN DERIVATIVES USEFUL AS METALLOPROTEINASE INHIBITORS

Related Applications

The present application is a U.S. National Phase Application of International Application No. PCT/GB2005/00004811 (filed Dec. 14, 2005) which claims the benefit of Great Britain Patent Application No. 427403.1 (filed Dec. 15, 2004), both of which are hereby incorporated by reference in their entirety.

The present invention relates to certain hydantoin derivatives useful in the inhibition of metalloproteinases, processes for their preparation, pharmaceutical compositions containing them, and their use in therapy.

The compounds of this invention are inhibitors of one or more metalloproteinase enzymes. Metalloproteinases are a superfamily of proteinases (enzymes) whose known numbers in recent years have increased dramatically. Based on structural and functional considerations these enzymes have been classified into families and subfamilies as described in N. M Hooper (1994) FEBS Letters 354:1-6. Examples of metalloproteinases include the matrixin family of matrix metalloproteinases (MMP) such as the collagenases (MMP1, MMP8, MMP13, MMP18), the gelatinases (MMP2, MMP9), the stromelysins (MMP3, MMP10, MMP11), the matrilysins (MMP7, MMP26), metalloelastase (MMP12), enamelysin (MP19), the membrane types MT-MMPs (MMP14, MMP15, MMP16, MMP17, MMP24, MMP25), and others (MMP20, MMP21, MMP22, MMP23a/b, MMP28); the ADAMs (a disintegrin, a metalloproteinase, also know as reprolysin or adamalysin or MDC) family which currently includes 32 known ADAMs with secretase and sheddase activity such as TNF converting enzyme (ADAM17), and 18 known ADAMTS (a disintegrin a metalloproteinase thrombospondin) including the aggrecanases (ADAMTS4, ADAMTS5); the astacin family which include enzymes such as procollagen processing proteinase (PCP); and other metalloproteinases such as the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265-279). Metalloproteinases have been associated with many disease conditions. Inhibition of the activity of one or more metalloproteinases may well be of benefit in these disease conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated where degradation outstrips synthesis of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as periodontitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atherosclerosis; and chronic obstructive pulmonary diseases, COPD.

A number of metalloproteinase inhibitors are known; different classes of compounds may have different degrees of potency and selectivity for inhibiting various metalloproteinases. The present inventors have discovered a new class of compounds that are inhibitors of metalloproteinases and are of particular interest in inhibiting collagenase 3 (also known as MMP-13). The compounds of this invention have superior potency and/or pharmacokinetic properties.

Collagenase 3 (MMP13) was initially cloned from a cDNA library derived from a breast tumour [J. M. P. Freije et al (1994) Journal of Biological Chemistry 269(24):16766-16773]. PCR-RNA analysis of RNAs from a wide range of tissues indicated that collagenase 3 (MMP13) expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation collagenase 3 (MMP13) has been detected in transformed epidermal keratinocytes [N. Johansson et al., (1997) Cell Growth Differ. 8(2):243-250], squamous cell carcinomas [N. Johansson et al., (1997) Am. J. Pathol. 151(2): 499-508] and epidermal tumours [K. Airola et al., (1997) J. Invest. Dermatol. 109(2):225-231]. These results are suggestive that collagenase 3 (MMP 13) is secreted by transformed epithelial cells and may be involved in the extracellular matrix degradation and cell-matrix interaction associated with metastasis especially as observed in invasive breast cancer lesions and in malignant epithelia growth in skin carcinogenesis.

Recent published data implies that collagenase 3 (MMP13) plays a role in the turnover of other connective tissues. For instance, consistent with collagenase 3 (MMP13) substrate specificity and preference for degrading type II collagen [P. G. Mitchell et al., (1996) J. Clin. Invest. 97(3):761-768; V. Knauper et al., (1996) The Biochemical Journal 271:1544-1550], collagenase 3 (MP13) has been hypothesised to serve a role during primary ossification and skeletal remodelling [M. Stahle-Backdahl et al., (1997) Lab. Invest. 76(5):717-728; N. Johansson et al., (1997) Dev. Dyn. 208(3):387-397], in destructive joint diseases such as rheumatoid and osteoarthritis [D. Wernicke et al., (1996) J. Rheumatol. 23:590-595; P. G. Mitchell et al., (1996) J. Clin. Invest. 97(3):761-768; O. Lindy et al., (1997) Arthritis Rheum 40(8):1391-1399]; and during the aseptic loosening of hip replacements [S. Imai et al., (1998) J. Bone Joint Surg. Br. 80(4):701-710]. Collagenase 3 (MMP13) has also been implicated in chronic adult periodontitis as it has been localised to the epithelium of chronically inflamed mucosa human gingival tissue [V. J. Uitto et al., (1998) Am. J. Pathol 152(6):1489-1499] and in remodelling of the collagenous matrix in chronic wounds [M. Vaalamo et al., (1997) J. Invest. Dermatol. 109(1):96-101].

Compounds which inhibit the action of metalloproteinases, in particular collagenase 3 (MMP 13) and MMP12 are described in WO 00/12478, WO 00/75108, WO 01/62742 and WO 02/074767. Included among these reported inhibitors are aryloxy piperidine sulfonylmethyl substituted hydantoin compounds in which the aryl ring is substituted by a number of possible substituents, including inter alia trifluoromethoxy.

There is no disclosure that the trifluoromethoxy substituent in such compounds may itself further be substituted.

Substituted alkoxy or aryloxy piperidine sulfonylmethyl substituted hydantoin compounds as inhibitors of matrix metalloproteinases are encompassed within the general disclosure of WO 02/074767. Among the numerous possible substituents for the alkoxy group listed is halogen. One of the disclosed compounds is (5S)-5-methyl-5-[({4-[4-(trifluoromethoxy)phenoxy]piperidin-1-yl}sulfonyl)methyl]imidazolidine-2,4-dione (Comparator Compound X).

The present inventors have found that substituted aryloxy piperidine sulfonylmethyl substituted hydantoin compounds in which the substituent is an C2-4alkoxy group which itself is substituted by two or more fluorine groups are particularly potent metalloproteinase inhibitors, especially of collagenase 3 (MMP13), and have desirable activity profiles.

According to the present invention there is provided a compound of the Formula (I)

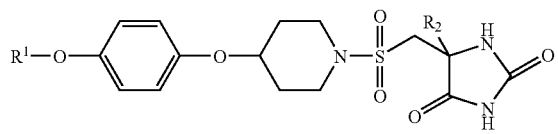

(I)

wherein
$R^1$ is a (2-4C)alkyl and is substituted by two or more fluorine groups; and
$R^2$ is methyl or ethyl;
or a pharmaceutically acceptable salt thereof.

In this specification, the term (2-4C)alkyl includes straight-chain and branched-chain alkyl groups such as ethyl, propyl, isopropyl, butyl, isobutyl and tert-butyl and the like. References to individual alkyl groups such as ethyl, propyl and butyl are specific for the straight-chain version.

A suitable pharmaceutically-acceptable salt of a compound of the Formula (I), for example, an acid-addition salt of a compound of the Formula I which is sufficiently basic, for example, an acid-addition salt with an inorganic or organic acid such as hydrochloric, hydrobromic, sulphuric, phosphoric, trifluoroacetic, citric, maleic, tartaric, fumaric, hemifumaric, succinic, hemisuccinic, mandelic, methanesulphonic, dimethanesulphonic, ethane-1,2-sulphonic, benzenesulphonic, salicylic or 4-toluenesulphonic acid, or, for example a salt of a compound of the Formula (I) which is sufficiently acidic, for example an alkali or alkaline earth metal salt such as a calcium or sodium salt, or an ammonium salt, or a salt with an organic base such as methylamine, dimethylamine, trimethylamine, piperidine, morpholine or tris-(2-hydroxyethyl)amine.

Where the compounds according to the invention contain one or more asymmetrically substituted carbon atoms, the invention includes all stereoisomers, including enantiomers and diastereomers, and mixtures including racemic mixtures thereof. Tautomers and mixtures thereof are also included.

Further values of $R^1$ and $R^2$ are as follows. Such values may be used where appropriate with any of the definitions, claims or embodiments defined hereinbefore or hereinafter.

$R^1$ is (2-4C)alkyl and is substituted by two or more fluorine groups.
$R^1$ is (2-4C)alkyl and is substituted by two to six fluorine groups.
$R^1$ is (2-4C)alkyl and is substituted by two to five fluorine groups.
$R^1$ is ethyl, propyl or butyl and is substituted by two or more fluorine groups.
$R^1$ is ethyl or propyl and is substituted by two or more fluorine groups.
$R^1$ is ethyl, propyl or butyl and is substituted by two to six fluorine groups.
$R^1$ is ethyl, propyl or butyl and is substituted by two to seven fluorine groups.
$R^1$ is ethyl or propyl and is substituted by two to six fluorine groups.
$R^1$ is ethyl or propyl and is substituted by two to five fluorine groups.
$R^1$ is CF3CH2-, CF2HCF2-, CF3CF2-, CF3CH2CH2-, CF2HCF2CH2- or CF3CF2CH2-.
$R^2$ is methyl or ethyl.
$R^2$ is methyl.
$R^2$ is ethyl.

Particular novel compounds of the invention include, for example, a compound of the Formula (I), or pharmaceutically-acceptable salts thereof, wherein:—
(a) $R^1$ is (2-4C)alkyl and is substituted by two or more fluorine groups; and $R^2$ is methyl.
(b) $R^1$ is (2-4C)alkyl and is substituted by two to six fluorine groups; and $R^2$ is methyl or ethyl.
(c) $R^1$ is ethyl, propyl or butyl and is substituted by two or more fluorine groups; and $R^2$ is methyl or ethyl.
(d) $R^1$ is ethyl, propyl or butyl and is substituted by two to six fluorine groups; and $R^2$ is methyl or ethyl.
(e) $R^1$ is ethyl or propyl and is substituted by two to five fluorine groups; and $R^2$ is methyl or ethyl.
(f) $R^1$ is CF3CH2-, CF2HCF2-, CF3CF2-, CF3CH2CH2-, CF2HCF2CH2- or CF3CF2CH2; and $R^2$ is methyl or ethyl.

A particular preferred compound of the invention is, for example:—
(5S)-5-methyl-5-[({4-[4-(2,2,2-trifluoroethoxy)phenoxy]piperidin-1-yl}sulfonyl)methyl]imidazolidine-2,4-dione;
(5S)-5-ethyl-5-[({4-[4-(2,2,2-trifluoroethoxy)phenoxy]piperidin-1-yl}sulfonyl)methyl]imidazolidine-2,4-dione;
5S-methyl-5-[({4-[4-(1,1,2,2-tetrafluoroethoxy)phenoxy]piperidin-yl}sulfonyl)methyl]imidazolidine-2,4-dione;
5S-ethyl-5-[({4-[4-(1,1,2,2-tetrafluoroethoxy)phenoxy]piperidin-1-yl}sulfonyl)methyl]imidazolidine-2,4-dione;
(5S)-5-methyl-5-[({4-[4-(pentafluoroethoxy)phenoxy]piperidin-1-yl}sulfonyl)methyl]imidazolidine-2,4-dione;
(5S)-5-ethyl-5-[({4-[4-(pentafluoroethoxy)phenoxy]piperidin-1-yl}sulfonyl)methyl]imidazolidine-2,4-dione;
5S-methyl-5-[({4-[3,3,3-trifluoropropoxy)phenoxy]piperidin-1-yl}sulfonyl)methyl]imidazolidine-2,4-dione;
5S-ethyl-5-[({4-[3,3,3-trifluoropropoxy)phenoxy]piperidin-1-yl}sulfonyl)methyl]imidazolidine-2,4-dione;
(5S)-5-methyl-5-[({4-[4-(2,2,3,3-tetrafluoropropoxy)phenoxy]-piperidin-1-yl}sulphonyl)methyl]imidazolidine-2,4-dione;
(5S)-5-ethyl-5-[({4-[4-(2,2,3,3-tetrafluoropropoxy)phenoxy]-piperidin-1-yl}sulphonyl)methyl]imidazolidine-2,4-dione;
(5S)-5-methyl-5-[({4-[4-(2,2,3,3,3-pentafluoropropoxy)phenoxy]-piperidin-1-yl}sulphonyl)methyl]imidazolidine-2,4-dione; and
(5S)-5-ethyl-5-[({4-[4-(2,2,3,3,3-pentafluoropropoxy)phenoxy]-piperidin-1-yl}sulphonyl)methyl]imidazolidine-2,4-dione.

Racemates may be separated into individual enantiomers using known procedures (cf. Advanced Organic Chemistry: 3rd Edition: author J March, p104-107). A suitable procedure involves formation of diastereomeric derivatives by reaction of the racemic material with a chiral auxiliary, followed by separation, for example by chromatography, of the diastereomers and then cleavage of the auxiliary species.

Without wishing to be limited by initial determinations, it is believed that in the present case the active enantiomer has S stereochemistry. This is based on comparison with related compounds for which the absolute configuration has been confirmed. Accordingly, the S-structure is shown in the formulae given in the examples below. It will be appreciated, however, that a racemate of any compound according to the invention can be resolved into the individual enantiomers by the method outlined above and the more active enantiomer can then be identified by a suitable assay, without the need to determine absolute configurations.

Compounds of the Formula I, or a pharmaceutically-acceptable salts thereof, may be prepared by any process known to be applicable to the preparation of chemically-related compounds. Suitable processes are illustrated by, for example, those in WO 02/074767. Such processes, when used to prepare a novel compound of the Formula I are provided as a farther feature of the invention and are illustrated by the following representative process variants in which, unless otherwise stated, $R^1$ and $R^2$ have any of the meanings defined hereinbefore. Necessary starting materials may be obtained by standard procedures of organic chemistry. The preparation of such starting materials is described in conjunction with the following representative process variants and within the accompanying Examples.

Alternatively necessary starting materials are obtainable by analogous procedures to those illustrated which are within the ordinary skill of an organic chemist.

A compound of the Formula I, or a pharmaceutically-acceptable salt thereof, may be prepared by reacting an phenoxy piperidine of the Formula II with a sulfonyl chloride of the Formula III

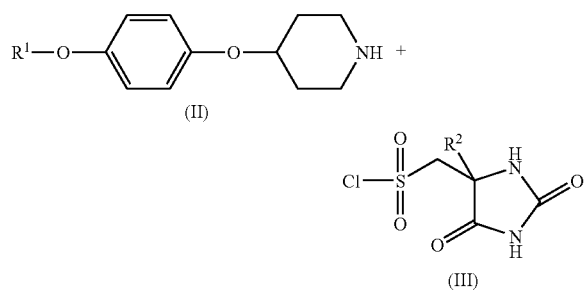

wherein $R^1$ and $R^2$ are as defined hereinbefore and wherein any functional group is protected if necessary, and:

(i) removing any protecting groups; and
(ii) optionally forming a pharmaceutically-acceptable salt.

The reaction is preferably performed in suitable solvent optionally in the presence of base for 1 to 24 hours at ambient to reflux temperature. Preferably, solvents such as pyridine, dimethylformamide, tetrahydrofuran, acetonitrile or dichloromethane are used with bases like triethylamine, N-methylmorpholine, pyridine or alkali metal carbonates at ambient temperature for 2-18 hours reaction time, or until end of reaction is achieved as detected by chromatographic or spectroscopic methods. Reactions of sulfonyl chlorides of formula III with various primary and secondary amines are previously described in the literature, and the variations of the conditions will be evident for those skilled in the art.

Synthesis of sulfonyl chlorides of formula III is described in the literature and can be prepared from e.g. cystein or homocystein (Mosher, J.:J. Org. Chem. 23,1257 (1958). Sulfonyl chlorides of formula III are also conveniently prepared according to Griffith, O.:J. Biol. Chem., 1983, 258, 3, 1591.

Compounds of the Formula (II) may be prepared according to Bioorg Med Chem 2003, 11 (3), 367 and Tet Lett 2002, 43 (12), 2157, using the appropriate fluoroalkoxyphenol and tert-butyl 4-hydroxy-1-piperidine carboxylate.

It will be appreciated that the preparation of compounds of formula (I) may involve, at various stages, the addition and removal of one or more protecting groups. The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of the invention are metalloproteinase inhibitors, in particular they are inhibitors of collagenase 3 (MMP 13) and therefore are indicated in the treatment of diseases or conditions mediated by metalloproteinase enzymes including arthritis (such as osteoarthritis), cancer, atherosclerosis and chronic obstructive pulmonary diseases (COPD) as discussed above. In particular, the compounds of the invention are indicated in the treatment of diseases or conditions mediated by collagenase 3 (MMP13). A particular advantage of the collagenase 3 inhibitors according to the invention is that they exhibit improved selectivity over other metalloproteinases.

According to a further aspect, therefore, the present invention provides a compound of formula (I), or a pharmaceutically acceptable salt thereof, as defined above for use in therapy of the human or animal body.

The invention also provides the use of a compound of formula (I), or a pharmaceutically acceptable salt thereof, as defined above, in the manufacture of a medicament for use in therapy.

It will be appreciated that "therapy" also includes "prophylaxis" unless otherwise indicated. The terms "therapeutic" and "therapeutically" will be understood accordingly.

In a yet further aspect the present invention provides a method of treating a metalloproteinase mediated disease condition which comprises administering to a warm-blooded animal a therapeutically effective amount of a compound of the formula (I) or a pharmaceutically acceptable salt thereof.

It will be appreciated that dosage administered will vary depending on the compound employed, the mode of administration, the treatment desired and the disorder indicated. Typically, a daily dose of 0.1 to 75 mg/kg body weight (and preferably of 0.1 to 30 mg/kg body weight) is received. This daily dose may be given in divided doses as necessary, the precise amount of the compound received and the route of administration depending on the weight, age and sex of the patient being treated and on the particular disease condition being treated according to principles known in the art.

The compounds of formula (I) and pharmaceutically acceptable salts thereof may be used on their own but will generally be administered in the form of a pharmaceutical composition in association with a pharmaceutically acceptable adjuvant, diluent or carrier.

The present invention therefore also provides a pharmaceutical composition comprising a compound of formula (I), or a pharmaceutically acceptable salt thereof in association with a pharmaceutically acceptable adjuvant, diluent or carrier.

The pharmaceutical compositions of the invention may be administered in standard manner for the disease condition that it is desired to treat, for example by oral, topical, parenteral, intra articular, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of the invention may also contain, or be co-administered (simultaneously or sequentially) with, one or more pharmacological agents of value in treating one or more disease conditions referred to above. Typically unit dosage forms will contain about 1 mg to 500 mg of a compound according to the invention.

The activity and selectivity of the compounds according to the invention may be determined using an appropriate enzyme inhibition test as described in WO 00/12478, WO 00/75108 and WO 01/62742. Collagenase 3 (MMP13) inhibitory activity may be assessed, for example, using the procedure set out below:—

Recombinant human proMMP13 (collagenase 3) may be expressed and purified as described by Knauper et al. [V. Knauper et al., (1996) The Biochemical Journal 271:1544-1550 (1996)]. The purified enzyme can be used to monitor inhibitors of activity as follows: purified proMMP13 is activated using 1 mM amino phenyl mercuric acid (APMA), 20 hours at 21° C.; the activated MMPP13 (11.25 ng per assay) is incubated for 4-5 hours at 35° C. in assay buffer (0.1M Tris-HCl, pH 7.5 containing 0.1M NaCl, 20 mM CaCl2, 0.02 mM ZnCl and 0.05% (w/v) Brij 35 using the synthetic substrate 7-methoxycoumarin-4-yl)acetyl.Pro.Leu.Gly.Leu.N-3-(2,4-dinitrophenyl)-L-2,3-diaminopropionyl.Ala.Arg.NH$_2$ in the presence or absence of inhibitors. Activity is determined by measuring the fluorescence at $\lambda$ex 328 nm and $\lambda$em 393 nm. By measuring the activity at a range of concentrations, a binding curve can be generated from which the IC50 can be determined, this figure being the inhibitor concentration at which the enzyme activity is reduced by 50%.

It will be appreciated that the pharmacological properties of the compounds of the invention will vary according to their structure but in general, compounds of the invention demonstrate collagenase 3 inhibitory activity as determined by the above assay at IC50 concentrations in the range 0.01 to 20 nM. The following table shows IC50 figures for a representative selection of compounds according to the invention, as well as for the Comparator Compound X disclosed in WO 02/074767, when tested in the above assay.

| Compound of Example No. | IC50 (nM) |
|---|---|
| Comparator Compound X | 59 |
| 1 | 8.5 |
| 2 | 8.4 |
| 3 | 5.0 |
| 4 | 4.9 |
| 5 | 9.8 |
| 6 | 13 |
| 7 | 5.4 |
| 8 | 5.5 |
| 9 | 1.1 |
| 10 | 0.7 |
| 11 | 2.0 |
| 12 | 1.9 |

A compound of the Formula I may be used in combination with other drugs and therapies used in the treatment of disease states which would benefit from the inhibition of metalloproteinases, in particular collagenase 3 (MMP13). For example, a compound of the Formula I could be used in combination with drugs and therapies used in the treatment of rheumatoid arthritis, asthma, cancer, inflammatory bowel disease, multiple sclerosis, AIDS, septic shock, congestive heart failure, ischaemic heart disease, psoriasis and the other disease states mentioned earlier in this specification.

For example, by virtue of its ability to inhibit metalloproteinases, a compound of the Formula I is of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I of the present invention with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

A compound of the Formula I may also be used with anti-inflammatory agents such as an inhibitor of the enzyme 5-lipoxygenase.

A compound of the Formula I may also be used in the treatment of conditions such as rheumatoid arthritis in combination with antiarthritic agents such as gold, methotrexate, steroids and pencillinamine, and in conditions such as osteoarthritis in combination with steroids.

A compound of the Formula I may also be administered in degradative diseases, for example osteoarthritis, with chondroprotective, anti-degradative and/or reparative agents such as Diacerhein, hyaluronic acid formulations such as Hyalan, Rumalon, Arteparon, chondroitin sulphate and glucosamine salts such as Antril.

A compound of the Formula I may be used in the treatment of asthma in combination with antiasthmatic agents such as steroids, bronchodilators and leukotriene antagonists.

In particular, for the treatment of the inflammatory diseases rheumatoid arthritis, osteoarthritis, psoriasis, inflammatory bowel disease, chronic obstructive pulmonary disease, asthma and allergic rhinitis a compound of the present invention may be combined with agents such as TNF-$\alpha$ inhibitors such as anti-TNF monoclonal antibodies (such as Remicade, CDP-870 and D.sub2.E.sub7.) and TNF receptor immunoglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold.

The present invention still further relates to the combination of a compound of the Formula I together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175;

Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY×1005.

The present invention still further relates to the combination of a compound of the Formula I together with a receptor antagonist for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the Formula I together with a PDE4 inhibitor including inhibitors of the isoform PDE4D.

The present invention still further relates to the combination of a compound of the Formula I together with a antihistaminic $H_1$ receptor antagonists such as cetirizine, loratadine, desloratadine, fexofenadine, astemizole, azelastine, and chlorpheniramine.

The present invention still further relates to the combination of a compound of the Formula I together with a gastroprotective $H_2$ receptor antagonist.

The present invention still further relates to the combination of a compound of the Formula I together with an $\alpha_1$- and $\alpha_2$-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the Formula I together with anticholinergic agents such as ipratropium bromide; tiotropium bromide; oxitropium bromide; pirenzepine; and telenzepine.

The present invention still further relates to the combination of a compound of the Formula I together with a $\beta_1$- to $\beta_4$-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the Formula I together with an insulin-like growth factor type I (IGF-1) mimetic.

The present invention still further relates to the combination of a compound of the Formula I together with an inhaled glucocorticoid with reduced systemic side effects, such as prednisone, prednisolone, flunisolide, triamcinolone acetonide, beclomethasone dipropionate, budesonide, fluticasone propionate, and mometasone faroate.

The present invention still further relates to the combination of a compound of the Formula I together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the C—$X_3$—C family.

The present invention still further relates to the combination of a compound of the Formula I together with antiviral agents such as Viracept, AZT, aciclovir and famciclovir, and antisepsis compounds such as Valant.

The present invention still further relates to the combination of a compound of the Formula I together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the Formula I together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the Formula I together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) inhibitors of cathepsins e.g. cathepsin B, cathepsin K, cathepsin L; (vii) MAP kinase inhibitors; (viii) glucose-6 phosphate dehydrogenase inhibitors; (ix) kinin-$B_1$- and $B_2$.-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) modulators of transforming growth factor (TGFβ); (xv) modulators of platelet-derived growth factor (PDGF); (xvi) modulators of fibroblast growth factor, e.g., basic fibroblast growth factor (bFGF); (xvii) modulators of granulocyte macrophage colony stimulating factor (GM-CSF); (xviii) capsaicin cream; (xix) Tachykinin $NK_1$ and $NK_3$ receptor antagonists selected from the group consisting of NKP-608C; SB-233412 (talnetant); and D-4418; (xx) elastase inhibitors selected from the group consisting of UT-77 and ZD-0892; (xxi) TNFα converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

A compound of the Formula I may also be used in combination with osteoporosis agents such as roloxifene, droloxifene, lasofoxifene or fosomax and immunosuppressant agents such as FK-506, rapamycin, cyclosporine, azathioprine, and methotrexate.

A compound of the Formula I may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

A compound of the Formula I can also be used in combination with existing therapeutic agents for the treatment of cancer. Suitable agents to be used in combination include:
(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) modulators of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

If formulated as a fixed dose such combination products employ a compound of the Formula I within the dosage range described herein and the other pharmaceutically-active agent within its approved dosage range. Sequential use is contemplated when a combination formulation is inappropriate.

Although a compound of the Formula I is primarily of value as a therapeutic agent for use in warm-blooded animals (including man), it is also useful whenever it is required to inhibit the effects of a metalloproteinase. Thus, it is useful as pharmacological standard for use in the development of new biological tests and in the search for new pharmacological agents.

The invention is further illustrated by the following non-limiting examples.

The relevant starting materials are commercially available or may be made by any convenient method as described in the literature or known to the skilled chemist or described in the examples herein. In addition the following table shows details of intermediates and their corresponding registry numbers in Chemical Abstracts.

| | Chemical Abstracts Registry Numbers |
|---|---|
| [(4S)-4-Methyl-2,5-dioxoimidazolidin-4-yl]methanesulfonyl chloride | 459818-50-9 |

EXAMPLE 1

(5S)-5-methyl-5-[({4-[4-(2,2,2-trifluoroethoxy)phenoxy]piperidin-1-yl}sulfonyl)methyl]imidazolidine-2,4-dione To a solution of 4-[4-(2,2,2-trifluoroethoxy)phenoxy]piperidine hydrochloride (0.3 g) and diisopropyl ethylamine (0.37 mL) in dichloromethane (100 mL) was added [(4S)-4-methyl-2,5-dioxoimidazolidin-4-yl]methanesulfonyl chloride (0.261 g). The resulting solution was stirred at ambient temperature for 18 hours.

The reaction solution was pre-adsorbed directly onto silica and purified by chromatography on a silica column eluted with ethyl acetate. The material obtained was triturated, filtered and washed with diethyl ether to yield (5S)-5-methyl-5-[({4-[4-(2,2,2-trifluoroethoxy)phenoxy]piperidin-1-yl}sulfonyl)methyl]imidazolidine-2,4-dione[0.33 g].

NMR Spectrum: (DMSOd$_6$) 1.15 (s, 3H), 1.6 (s, 2H), 1.8 (m, 2H), 3.1 (m, 2H), 3.2-3.6 (m, 4H), 4.4 (m, 1H), 4.6-4.7 (m, 2H), 6.9 (m, 4H), 8.9 (s, 1H) 10.7 (Broad, 1H), Mass Spectrum: M−H⁻ 464.

The corresponding starting material was synthesized as follows;

To a solution of 4-benzyloxyphenol (10 g), tert-butyl 4-hydroxy-1-piperidine carboxylate (11 g) and triphenylphosphine (19.7 g), in dichloromethane (300 mL), was added a solution of diisopropyldiazodicarboxylate (14.8 mL), in dichloromethane (15 mL), drop wise over 15 minutes. The reaction was heated to reflux for 4 hours.

The solvent was removed. The residue stirred with 20% ethyl acetate/isohexane (250 mL) and triphenylphosphine oxide filtered off. The filtrate was evaporated and redissolved in dichloromethane (100 mL) and pre adsorbed onto silica. Purification was carried out using a silica pad using gradient elution with 2-20% ethyl acetate/isohexane. The isolated material was triturated with 10% diethyl ether/isohexane (100 mL) to yield tert-butyl 4-[4-(benzyloxy)phenoxy]piperidine-1-carboxylate (12.2 g). NMR Spectrum: (DMSOd$_6$) 1.4 (s, 9H), 1.5 (m, 2H), 1.8 (m, 2H), 3.1 (m, 2H), 3.6 (m, 2H), 4.4 (m, 1H), 5.0 (s, 2H), 6.9 (m, 4H), 7.3-7.5 (m, 5H). Mass Spectrum: M−H⁻ 284.

To 10% palladium on carbon (0.75 g), under a stream of argon, was added a solution of tert-butyl 4-[4-(benzyloxy) phenoxy]piperidine-1-carboxylate (7.5 g) in ethanol (250 mL). The vessel was purged with argon three times, before hydrogen was introduced to the system via a balloon. The reaction was stirred vigorously at ambient temperature for 3 hours. Hydrogen was removed from the system and purged three times with argon before filtering through a celite pad. The pad was washed thoroughly. The filtrate and washings were combined and evaporated, the solid triturated with 20% diethyl ether/iso-hexane to yield tert-butyl-4-hydroxy-1-piperidinecarboxylate (5.7 g) NMR Spectrum: (CDCl$_3$) 1.5 (s, 9H), 1.7 (m, 2H), 1.9 (m, 2H), 3.3 (m, 2H), 3.7 (m, 2H), 4.3 (m, 1H), 4.8 (s, 1H), 6.7 (m, 4H).

To a suspension of tert-butyl-4-hydroxy-1-piperidinecarboxylate (4 g) and freshly ground potassium carbonate (4.2 g) in acetone (200 ml) was added neat 2,2,2-trifluoroethyl nonafluorobutane sulphonate (6.7 g) and allowed to stir for 3 hours at ambient temperature. After 4 hours a further addition of nonaflate (3.3 g) was carried out and the temperature raised to reflux for 18 hours.

The potassium carbonate was filtered off, the residue evaporated and dissolved in ethyl acetate (200 ml), washed with water (100 ml) and saturated brine (100 ml), dried over magnesium sulphate and evaporated to produce a crude white solid which was purified by chromatography on silica eluting with 20% ethyl acetate/iso-hexane to yield tert-butyl 4-[4-(2,2,2-trifluoroethoxy)phenoxy]piperidine-1-carboxylate (3 g). NMR Spectrum: (CDCl$_3$) 1.45 (s, 9H), 1.7 (m, 2H), 1.9 (m, 2H), 3.3 (m, 2H), 3.7 (m, 2H), 4.3 (m, 3H), 6.85 (m, 4H).

To tert-butyl 4-[4-(2,2,2-trifluoroethoxy)phenoxy]piperidine-1-carboxylate (3 g) was added 4 molar hydrogen chloride in 1,4-dioxane (50 ml), stirred at ambient temperature for 1 hour. The solvent was removed and the resultant solid triturated and washed twice with a small amount of diethyl ether to yield 4-[4-(2,2,2-trifluoroethoxy)phenoxy]piperidine as a hydrochloride salt (2.4 g). NMR Spectrum: (DMSOd$_6$) 1.7 (m, 2H), 2.0 (m, 2H), 3.0 (m, 2H), 3.2 (m, 2H), 4.5 (m, 1H), 4.6 (m, 2H), 6.9 (m, 4H), 8.8 (broad, 2H). Mass Spectrum: M−H⁻ 276.

EXAMPLE 2

(5S)-5-ethyl-5-[({4-[4-(2,2,2-trifluoroethoxy)phenoxy]piperidin-1-yl}sulfonyl)methyl]imidazolidine-2,4-dione

[(4S)-4-ethyl-2,5-dioxoimidazolidin-4-yl]methanesulfonyl chloride (WO 2004/024698) (869 mg) was added to a stirred solution of 4-[4-(2,2,2-trifluoroethoxy)phenoxy]piperidine hydrochloride (750 mg) and triethylamine (1.68 ml) in dichloromethane (50 ml) and the reaction stirred at ambient temperature for 2 hours. The solvents were removed in vacuo and the residue stirred in water for 2 hours. The resulting solid was filtered off, washed with water then ether and dried to give the title compound (1.13 g); NMR Spectrum: (DMSOd$_6$) 0.78 (t, 3H), 1.25 (m, 2H), 1.66 (m, 4H), 1.94 (m, 2H), 3.11 (m, 2H), 3.49 (d, 1H), 3.58 (m, 1H), 4.41 (m, 1H), 4.64 (q, 2H), 6.97 (m, 4H), 8.5 (s, 1H), 10.71 (s, 1H); Mass Spectrum: M−H⁻ 478.

EXAMPLE 3

5S-methyl-5-[({4-[4-(1,1,2,2-tetrafluoroethoxy)phenoxy]piperidin-yl}sulfonyl)methyl]imidazolidine-2,4-dione Diisopropylethylamine (0.35 mL) and (4S-methyl-2,5-dioxoimidazolidin-4-yl)methanesulfonyl chloride (248 mg) was added to a suspension of 4-[4-(1,1,2,2-tetrafluoroethoxy) phenoxy]piperidine (300 mg) in dichloromethane (50 mL). The mixture was stirred at ambient temperature for 18 hours. The mixture was then pre-absorbed onto silica gel at reduced pressure and purified by silica column chromatography, eluting with ethyl acetate. The isolated product was then recrystallised from ethanol (5 mL) and filtered. The solid was then stirred in diethyl ether, filtered and dried under vacuum to give the title compound as a white solid (245 mg); NMR Spectrum: (DMSOd$_6$) 1.34 (s, 3H), 1.66-1.78 (m, 2H), 1.92-2.04 (m, 2H), 3.08-3.20 (m, 2H), 3.31-3.42 (m, 2H), 3.35 (d, 1H), 3.52 (d, 1H), 4.50-4.60 (m, 1H), 6.76 (tt, 1H), 7.06 (d, 2H), 7.20 (d, 2H), 7.98 (s, 1H), 10.72 (s. 1H); Mass Spectrum: M−H⁻ 482.

4-[4-(1,1,2,2-tetrafluoroethoxy)phenoxy]piperidine was prepared as follows: Diisopropyl azodicarboxylate (2.25 mL) was added to a solution of 4-(1,1,2,2-tetrafluoroethoxy)phenol (2.0 g), tert-butyl 4 hydroxypiperidine-1-carboxylate (2.3 g) and triphenylphosphine (3.5 g) in dichloromethane (30 mL). The reaction mixture was stirred at ambient temperature for 18 hours and then concentrated at reduced pressure. This resulting mixture was purified by silica column chromatography, eluting with a gradient of 0 to 15% ethyl acetate in hexane to give the tert-butyl 4-[4-(1,1,2,2-tetrafluoroethoxy) phenoxy]piperidine-1-carboxylate as a light green oil (3.3 g); NMR Spectrum: (DMSOd$_6$) 1.39 (s, 9H), 1.43-1.57 (m, 2H), 1.82-1.95 (m, 2H), 3.09-3.24 (m, 2H), 3.56-3.70 (m, 2H), 4.47-4.59 (m, 1H), 6.73 (tt, 1H), 7.03 (d, 2H), 7.16 (d, 2H).

4M HCl in dioxane (30 mL) was added to tert-butyl 4-[4-(1,1,2,2-tetrafluoroethoxy)phenoxy]piperidine-1-carboxylate (3.3 g). The mixture was stirred at ambient temperature for 30 minutes. The mixture was then concentrated at reduced pressure and triturated with diethyl ether. The resulting precipitate was filtered, washed with diethyl ether and dried under vacuum to give 4-[4-(1,1,2,2-tetrafluoroethoxy)phenoxy]piperidine as the hydrochloride salt (2.76 g); NMR Spectrum: (DMSOd$_6$) 1.75-1.91 (m, 2H), 2.02-2.17 (m, 2H), 2.95-3.12 (m, 2H), 3.13-3.29 (m, 2H), 4.57-4.69 (m, 1H), 6.75 (tt, 1H), 7.06 (d, 2H), 7.19 (d, 2H), 8.95 (bs, 2H); Mass Spectrum: M+H⁺ 294.

EXAMPLE 4

5S-ethyl-5-[({4-[4-(1,1,2,2-tetrafluoroethoxy)phenoxy]piperidin-yl}sulfonyl)methyl]imidazolidine-2,4-dione Diisopropylethylamine (0.35 mL) and (4S-ethyl-2,5-dioxoimidazolidin-4-yl)methanesulfonyl chloride (262 mg) was added to a suspension of 4-[4-(1,1,2,2-tetrafluoroethoxy) phenoxy]piperidine (300 mg) in dichloromethane (50 mL). The mixture was stirred at ambient temperature for 18 hours. The mixture was then pre-absorbed onto silica gel at reduced pressure and purified by silica column chromatography, eluting with ethyl acetate. The isolated product was then recrystallised from ethanol (5 mL) and filtered. The solid was then stirred in diethyl ether, filtered and dried under vacuum to give the title compound as a white solid (250 mg); NMR Spectrum: (DMSOd$_6$) 0.78 (t, 3H), 1.60-1.79 (m, 2H), 1.65 (q, 2H), 1.90-2.09 (m, 2H), 3.09-3.20 (m, 2H), 3.31-3.42 (m, 2H), 3.35 (d, 1H), 3.50 (d, 1H), 4.50-4.60 (m, 1H), 6.76 (tt, 1H), 7.06 (d, 2H), 7.20 (d, 2H), 7.95 (s, 1H), 10.74 (s, 1H); Mass Spectrum: M−H$^-$ 496.

EXAMPLE 5

(5S)-5-methyl-5-[({4-[4-(pentafluoroethoxy)phenoxy]piperidin-1-yl}sulfonyl)methyl]imidazolidine-2,4-dione To a solution of 4-[4-(pentafluoroethoxy)phenoxy]piperidine hydrochloride (0.15 g) and diisopropylethylamine (0.19 mL) in dichloromethane (100 mL) was added [(4S)-4-methyl-2,5-dioxoimidazolidin-4-yl]methanesulfonyl chloride (0.12 g). The reaction was stirred at ambient temperature for 18 hours.

The reaction solution was purified directly using column chromatography eluting with a gradient of 1 to 5% methanol in dichloromethane. The material obtained was triturated with a small volume of 50% ethanol/diethyl ether. The resultant solid washed with diethyl ether, filtered and dried under vacuum to give the title compound (0.18 g); NMR Spectrum: (DMSOd$_6$) 1.0 (m, 3H), 1.35 (s, 3H), 1.7 (m, 2H), 1.9 (m, 2H), 3.1 (m, 2H), 3.3-3.5 (m, 4H), 4.5 (m, 1H), 7.05 (m, 2H), 7.25 (m, 2H) 8.0 (s, 1H), 10.7 (s, 1H); Mass Spectrum: M−H$^-$ 500.

The 4-[4-(pentafluoroethoxy)phenoxy]piperidine hydrochloride used as a starting material was prepared as follows:—

To a solution of 4-(1,1,2,2,2-pentafluoroethoxy)phenol (6.5 g), tert-butyl-4-hydroxy-1-piperidinecarboxylate (6.3 g), triphenylphosphine (11.2 g), in dichloromethane (400 mL) was added neat diisopropyldiazodicarboxylate (5.6 mL) drop wise over 5 minutes. The reaction was then heated to reflux for 18 hours.

The reaction solution was pre-adsorbed onto silica and purified using column chromatography eluting with 1:4 mixture of ethyl acetate and isohexane to yield tert-butyl 4-[4-(pentafluoroethoxy)phenoxy]piperidine-1-carboxylate (3.9 g) NMR Spectrum: (CDCl$_3$) 1.2 (s, 9H), 1.5 (m, 2H), 1.8 (m, 2H), 3.1 (m, 2H), 3.6 (m, 2H), 4.6 (m, 1H), 7.05 (m, 2H), 7.25 (m, 2H); Mass Spectrum: M-$^t$Bu$^-$ 354.

tert-butyl 4-[4-(pentafluoroethoxy)phenoxy]piperidine-1-carboxylate (3.8 g) was stirred in 4.0M HCl in 1,4-dioxane (50 mL) for 1 hour. The solvent was removed the resulting solid triturated with diethyl ether (50 mL), filtered and washed with diethyl ether (2×50 mL) to yield 4-[4-(pentafluoroethoxy)phenoxy]piperidine hydrochloride as a white solid (2.9 g) NMR Spectrum: (CDCl$_3$) 2.1 (m, 2H), 2.3 (m, 2H), 3.3 (m, 4H), 4.6.(s, 1H), 6.9 (m, 2H), 7.2 (m, 2H), 9.8 (broad, 1H); Mass Spectrum: M−H$^-$ 312

EXAMPLE 6

(5S)-5-ethyl-5-[({4-[4-(pentafluoroethoxy)phenoxy]piperidin-1-yl}sulfonyl)methyl]imidazolidine-2,4-dione To a solution of 4-[4-(pentafluoroethoxy)phenoxy]piperidine hydrochloride (0.17 g) and diisopropylethylamine (0.19 mL) in dichloromethane (100 mL) was added [(4S)-4-ethyl-2,5-dioxoimidazolidin-4-yl]methanesulfonyl chloride (0.13 g). The reaction was stirred at ambient temperature for 18 hours.

The reaction solution was purified directly using column chromatography eluting with a gradient of 1 to 5% methanol in dichloromethane. The material obtained was triturated with a small volume of 50% ethanol/diethyl ether. The resultant solid washed with diethyl ether, filtered and dried under vacuum to give the title compound (0.17 g); NMR Spectrum:_(DMSOd$_6$) 0.8 (m, 3H), 1.2 (s, 2H), 1.7 (m, 2H), 1.8 (m, 2H), 2.0 (m, 2H), 3.1 (m, 2H), 3.3-3.5 (m, 4H), 4.6 (m, 1H), 7.1 (m, 2H), 7.25 (m, 2H) 7.9 (s, 1H), 10.7 (s, 1H); Mass Spectrum: M−H$^-$ 514.

EXAMPLE 7

5S-methyl-5-[({4-[3,3,3-trifluoropropoxy)phenoxy]piperidin-1-yl}sulfonyl)methyl]imidazolidine-2,4-dione Diisopropylethylamine (0.37 mL) and (4S-methyl-2,5-dioxoimidazolidin-4-yl)methanesulfonyl chloride (117 mg) was added to a suspension of 4-[4-(3,3,3-trifluoropropoxy)phenoxy]piperidine hydrochloride (140 mg) in methylene chloride (20 mL). The mixture was stirred at ambient temperature for 18 hours. The reaction was incomplete so (4S-methyl-2,5-dioxoimidazolidin-4-yl)methanesulfonyl chloride (50 mg) was added. The mixture was stirred at ambient temperature for 4 hours. The mixture was then concentrated at reduced pressure and purified by silica column chromatography, eluting with a gradient of 0 to 5% methanol in dichloromethane. The isolated product was then purified by silica column chromatography, eluting with a gradient of 0 to 100% ethyl acetate in hexane to give the title compound as a white solid (90 mg); NMR Spectrum: (DMSOd$_6$) 1.34 (s, 3H), 1.63-1.75 (m, 2H), 1.87-1.98 (m, 2H), 2.65-2.82 (m, 2H), 3.06-3.19 (m, 2H), 3.30-3.41 (m, 2H), 3.34 (d, 1H), 3.51 (d, 1H), 4.15 (t, 2H), 4.35-4.45 (m, 1H), 6.87-6.98 (m, 4H), 7.98 (s, 1H), 10.71 (s, 1H); Mass Spectrum: M−H$^-$ 478.

The starting material 4-[4-(3,3,3-trifluoropropoxy)phenoxy]piperidine was prepared as follows:

Diisopropyl azodicarboxylate (2.36 mL) was added to a solution of 4-(benzyloxy)phenol (2.0 g), tert-butyl 4 hydroxypiperidine-1-carboxylate (2.41 g) and triphenylphosphine (3.67 g) in dichloromethane (30 mL). The reaction mixture was stirred at ambient temperature for 18 hours and then concentrated at reduced pressure. This resulting mixture was purified by silica column chromatography, eluting with a gradient of 0 to 20% ethyl acetate in hexane to give tert-butyl 4-[4-(benzyloxy)phenoxy]piperidine-1-carboxylate as a light orange oil (3.25 g); NMR Spectrum: (CDCl$_3$) 1.47 (s, 9H), 1.65-1.77 (m, 2H), 1.83-1.93 (m, 2H), 3.24-3.34 (m, 2H), 3.65-3.76 (m, 2H), 4.27-4.35 (m, 1H), 5.01 (s, 2H), 6.80-6.93 (m, 4H), 7.28-7.45 (m, 5H); Mass Spectrum: (M-$^t$BuOCO)+H$^+$ 284.

10% Palladium on carbon (0.75 g, 50% w/w) was added to a solution of tert-butyl 4-[4-(benzyloxy)phenoxy]piperidine-1-carboxylate (1.5 g) in ethanol (100 mL). The mixture was evacuated and purged with hydrogen twice and then stirred under an atmosphere of hydrogen for 2 hours. The mixture was filtered through celite and the filter pad washed with ethanol. The filtrate was concentrated at reduced pressure to give tert-butyl 4-(hydroxyphenoxy)piperidine-1-carboxylate as a brown solid (1.24 g); NMR Spectrum: (CDCl$_3$) 1.47 (s, 9H), 1.65-1.76 (m, 2H), 1.82-1.93 (m, 2H), 3.23-3.33 (m, 2H), 3.65-3.76 (m, 2H), 4.25-4.34 (m, 1H), 5.07 (s, 1H), 6.70-6.85 (m, 4H).

Diisopropyl azodicarboxylate (0.97 mL) was added to a solution of tert-butyl 4-(hydroxyphenoxy)piperidine-1-carboxylate (1.2 g), 3,3,3-trifluoro-1-propanol (0.56 g) and triphenylphosphine (1.5 g) in dichloromethane (15 mL). The reaction mixture was stirred at ambient temperature for 18 hours and then concentrated at reduced pressure. This resulting mixture was purified by silica column chromatography, eluting with a gradient of 0 to 15% ethyl acetate in hexane to give tert-butyl 4-[4-(3,3,3-trifluoropropoxy)phenoxy]piperidine-1-carboxylate as a white solid (0.6 g); NMR Spectrum: (CDCl$_3$) 1.47 (s, 9H), 1.66-1.77 (m, 2H), 1.83-1.94 (m, 2H), 2.52-2.66 (m, 2H), 3.24-3.34 (m, 2H), 3.65-3.75 (m, 2H), 4.11 (t, 2H), 4.27-4.37 (m, 1H), 6.78-6.89 (m, 4H); Mass Spectrum: M+H$^+$ 390 and (M-$^t$BuOCO)+H$^+$ 290.

4M HCl in dioxane (10 mL) was added to tert-butyl 4-[4-(3,3,3-trifluoropropoxy)phenoxy]piperidine-1-carboxylate (550 mg). The mixture was stirred at ambient temperature for 10 minutes. The mixture was then concentrated at reduced pressure and triturated with diethyl ether and stirred for 10 minutes. The resulting precipitate was filtered and dried under vacuum to give 4-[4-(3,3,3-trifluoropropoxy)phenoxy]piperidine as the hydrochloride salt (286 mg); NMR Spectrum: (DMSOd$_6$) 1.76-1.88 (m, 2H), 2.01-2.12 (m, 2H), 2.66-2.82 (m, 2H), 2.97-3.10 (m, 2H), 3.14-3.27 (m, 2H), 4.15 (t, 2H), 4.46-4.56 (m, 1H), 6.87-6.98 (m, 4H), 9.03 (bs, 2H); Mass Spectrum: M+H$^+$ 290.

EXAMPLE 8

5S-ethyl-5-[({4-[3,3,3-trifluoropropoxy)phenoxy]piperidin-1-yl}sulfonyl)methyl]imidazolidine-2,4-dione Diisopropylethylamine (0.37 mL, 2.12 mmol) and (4S-ethyl-2,5-dioxoimidazolidin-4-yl)methanesulfonyl chloride (124 mg, 0.52 mmol) was added to a suspension of 4-[4-(3,3,3-trifluoropropoxy)phenoxy]piperidine hydrochloride (140 mg) in dichloromethane (20 mL). The mixture was stirred at ambient temperature for 18 hours. The reaction was incomplete so (4S-ethyl-2,5-dioxoimidazolidin-4-yl)methanesulfonyl chloride (50 mg) was added. The mixture was stirred at ambient temperature for 4 hours. The mixture was then concentrated at reduced pressure and purified by silica column chromatography, eluting with a gradient of 0 to 5% methanol in methylene chloride. The isolated product was then purified by silica column chromatography, eluting with a gradient of 0 to 100% ethyl acetate in hexane to give the title compound as a white solid (90 mg); NMR Spectrum: (DMSOd$_6$) 0.78 (t, 3H), 1.60-1.65 (m, 2H), 1.65 (q, 2H), 1.88-1.98 (m, 2H), 2.66-2.81 (m, 2H), 3.06-3.16 (m, 2H), 3.30-3.40 (m, 2H), 3.33 (d, 1H), 3.49 (d, 1H), 4.15 (t, 2H), 4.36-4.45 (m, 1H), 6.87-6.97 (m, 4H), 7.95 (s, 1H), 10.73 (s, 1H); Mass Spectrum: M−H$^-$ 492.

EXAMPLE 9

(5S)-5-methyl-5-[({4-[4-(2,2,3,3-tetrafluoropropoxy)phenoxy]-piperidin-1-yl}sulphonyl)methyl]imidazolidine-2,4-dione

[(4S)-4-methyl-2,5-dioxoimidazolidin-4-yl]methanesulphonyl chloride (0.453 g) was added to a solution of 4-{4-(2,2,3,3-tetrafluoropropoxy)phenoxy]-piperidine hydrochloride (0.69 g) in dichloromethane (25 ml) and triethylamine (1.7 ml) at ambient temperature. Stirred for 16 hours and evaporated to dryness. The residue was purified by column chromatography (using λ230 nm as the detecting wavelength) eluting with a 0-10% methanol and dichloromethane. Yielded a solid product, which was dried under vacuum at 50° C. to yield the title compound (0.24 g). NMR Spectrum: (DMSOd$_6$) δ 10.7 (s, 1H), 8.0 (s, 1H), 6.95 (m, 4H), 6.6 (tt, 1H), 4.5 (m, 2H), 4.4 (m, 1H), 3.5 (d, 1H), 3.3 (m, 3H), 3.1 (m, 2H), 1.9 (m, 2H), 1.7 (m, 2H), 1.35 (s, 3H). Mass Spectrum M−H$^-$ 495.89

The 4-{4-(2,2,3,3-tetrafluoropropoxy)phenoxy]-piperidine hydrochloride used as starting material was prepared as follows:—

2,2,3,3-Tetrafluoropropanol (2.64 g) was added to a suspension of sodium hydride (1.08 g) in dry ether (50 ml) at 0° C. under an argon atmosphere. Stirred at 0° C. for 15 minutes. Perfluoro-1-butanesulphonyl fluoride (12.08 g) was slowly added. Stirred at reflux for 3 hours, cooled and carefully quenched with H$_2$O. Extracted with ether, twice. The combined extracts were washed with saturated brine, dried over MgSO$_4$, filtered and evaporated to give 2,2,3,3-tetrafluoropropyl-1,1,2,2,3,3,4,4,4-nonafluorobutane-1-sulphonate as an oil. Yield 5.47 g. NMR Spectrum: (CDCl$_3$) δ 5.9 (tt, 1H), 4.75 (t, 2H).

2,2,3,3-tetrafluoropropyl-1,1,2,2,3,3,4,4,4-nonafluorobutane-1-sulphonate (4.84 g) was dissolved in acetone (50 ml). Tert-butyl 4-(4-hydroxyphenoxy)piperidine-1-carboxylate (1.71 g) and potassium carbonate (2.42 g) were added and stirred at ambient temperature for 16 hours. Filtered off the insoluble material and evaporated the filtrate to dryness to yield an oil. Purified by column chromatography using 0-25% ethyl acetate/iso-hexane as eluent. Yielded tert-butyl-4-[4-(2,2,3,3-tetrafluoropropoxy)phenoxy]piperidine-1-carboxylate, 2.66 g as an oil. NMR Spectrum: (CDCl$_3$) δ 6.85 (m, 4H), 6.0 (tt, 1H), 4.6 (m, 2H), 4.26 (m, 1H), 3.7 (m, 2H), 3.3 (m, 2H), 1.85 (m, 2H), 1.7 (m, 2H), 1.45 (s, 9H). Tert-butyl-4-[4-(2,2,3,3-tetrafluoropropoxy)phenoxy]piperidine-1-carboxylate (2.66 g) was dissolved in 1,4-dioxane (25 ml) and 4M HCl in 1,4-dioxane (9.75 ml) was added. Stirred at ambient temperature for 16 hours. The reaction mixture was evaporated to dryness to yield a white solid. The solid was triturated with ether, isolated and dried under vacuum at 50° C. Yielded 4-{4-(2,2,3,3-tetrafluoropropoxy)phenoxy]-piperidine hydrochloride as a solid 1.38 g NMR Spectrum: (DMSOd$_6$) δ 9.0 (br, 1H), 7.0 (m, 4H), 6.65 (tt, 1H), 4.52 (m, 2H), 4.4 (m, 1H), 3.2 (m, 2H), 3.05 (m, 2H), 2.1 (m, 2H), 1.8 (m, 2H). Mass Spectrum M+H$^+$ 308

EXAMPLE 10

(5S)-5-ethyl-5-[({4-[4-(2,2,3,3-tetrafluoropropoxy)phenoxy]-piperidin-1-yl}sulphonyl)methyl]imidazolidine-2,4-dione An analogous procedure to that described in example 9 was used to make the title compound, using [(4S)-4-ethyl-2,5-dioxoimidazolidin-4-yl]methanesulphonyl chloride, on the same scale. Yield 136 mg. NMR Spectrum: (DMSOd$_6$) δ 10.8 (s, 1H), 7.95 (s, 1H), 6.95 (m, 4H), 6.7 (tt, 1H), 4.5 (m, 2H), 4.4 (m, 1H), 3.5 (d, 1H), 3.3 (m, 3H), 3.1 (m, 2H), 1.9 (m, 2H), 1.65 (m, 4H), 0.8 (t, 3H). Mass Spectrum: M−H$^-$ 510.

EXAMPLE 11

(5S)-5-methyl-5-[({4-[4-(2,2,3,3,3-pentafluoropropoxy)phenoxy]-piperidin-1-yl}sulphonyl)methyl]imidazolidine-2,4-dione

[(4S)-4-methyl-2,5-dioxoimidazolidin-4-yl]methanesulphonyl chloride (0.188 g) was added to a solution of 4-{4-(2,2,3,3,3-pentafluoropropoxy)phenoxy]-piperidine hydrochloride (0.30 g) in dichloromethane (10 ml) and triethylamine (0.70 ml) at ambient temperature. Stirred for 16 hours and evaporated to dryness. The residue was purified by prep HPLC (using λ230 nm as the detecting wavelength) eluting with 0-95% acetonitrile, H$_2$O, +0.2% trifluoroacetic acid. Yielded a solid product, which was dried under vacuum at 50° C. to give the title compound (0.076 g). NMR: (DMSOd$_6$) δ 10.7 (s, 1H), 8.0 (s, 1H), 7.0 (m, 4H), 4.75 (t, 2H), 4.45 (m, 1H), 3.5 (d, 1H), 3.3 (m, 3H), 3.1 (m, 2H), 1.95 (m, 2H), 1.7 (m, 2H), 1.35 (s, 3H). Mass Spectrum: M–H⁻ 513.

The 4-{4-(2,2,3,3,3-pentafluoropropoxy)phenoxy]-piperidine hydrochloride used as starting material was prepared as follows:—

2,2,3,3,3-pentafluoropropanol (3.0 g) was added to a suspension of sodium hydride (1.08 g) in dry ether (50 ml) at 0° C. under an argon atmosphere. Stirred at 0° C. for 15 minutes. Perfluoro-1-butanesulphonyl fluoride (12.08 g) was slowly added. Stirred at reflux for 3 hours, cooled and carefully quenched with H$_2$O. Extracted with ether, twice. The combined extracts were washed with saturated brine dried over MgSO$_4$, filtered and evaporated to give 2,2,3,3,3-pentafluoropropyl-1,1,2,2,3,3,4,4,4-nonafluorobutane-1-sulphonate as an oil. Yield 7.9 g. NMR: (CDCl$_3$) δ 4.9 (m, 2H).

2,2,3,3,3-pentafluoropropyl-1,1,2,2,3,3,4,4,4-nonafluorobutane-1-sulphonate (6.7 g) was dissolved in acetone (75 ml). Tert-butyl 4-(4-hydroxyphenoxy)piperidine-1-carboxylate (2.34 g) and potassium carbonate (3.31 g) were added Stirred at ambient temperature for 16 hours. Filtered off the insoluble material and evaporated the filtrate to dryness to yield an oil. Purified by column chromatography using 0-20% ethyl acetate/iso-hexane as eluent. Yielded tert-butyl-4-[4-(2,2,3,3,3-pentafluoropropoxy)phenoxy]piperidine-1-carboxylate, 0.81 g as an oil. NMR Spectrum: (CDCl$_3$) δ 6.35 (m, 4H), 3.8 (m, 3H), 3.2 (m, 2H), 2.8 (m, 2H), 1.3 (m, 2H), 1.2 (m, 2H), 0.9 (s, 9H).

Tert-butyl-4-[4-(2,2,3,3,3-pentafluoropropoxy)phenoxy] piperidine-1-carboxylate (0.81 g) was dissolved in 4M HCl in 1,4-dioxane (10 ml) was added. Stirred at ambient temperature for 16 hours. The reaction mixture was evaporated to dryness to yield a white solid. The solid was triturated with ether, isolated and dried under vacuum at 50° C. Yielded 4-{4-(2,2,3,3,3-pentafluoropropoxy)phenoxy]-piperidine hydrochloride as a solid 0.76 g. NMR Spectrum (DMSOd$_6$) δ 9.0 (br, 1H), 7.0 (m, 4H), 4.7 (m, 2H), 4.5 (m, 1H), 3.2 (m, 2H), 3.0 (m, 2H), 2.05 (m, 2H), 1.8 (m, 2H). Mass Spectrum M+H⁺ 326

EXAMPLE 12

(5S)-5-ethyl-5-[({4-[4-(2,2,3,3,3-pentafluoropropoxy)phenoxy]-piperidin-1-yl}sulphonyl)methyl] imidazolidine-2,4-dione An analogous procedure to that described in example 11 was used to make the title compound, using [(4S)-4-ethyl-2,5-dioxoimidazolidin-4-yl]methanesulphonyl chloride, on the same scale. Yield 0.85 g. NMR Spectrum (DMSOd$_6$) δ 10.8 (s, 1H), 7.95 (s, 1H), 6.95 (m, 4H), 6.7 (tt, 1H), 4.5 (m, 2H), 4.4 (m, 1H), 3.5 (d, 1H), 3.3 (m, 3H), 3.1 (m, 2H), 1.9 (m, 2H), 1.65 (m, 4H), 0.8 (t, 3H).

What we claim is:

1. A compound of the Formula (I)

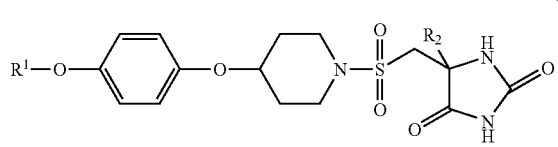

(I)

wherein
R$^1$ is a (2-4C)alkyl and is substituted by two or more fluorine groups; and
R$^2$ is methyl or ethyl;
or a pharmaceutically acceptable salt thereof.

2. The compound of the Formula (I) as claimed in claim 1 wherein R$^1$ is ethyl, propyl or butyl and is substituted by two or more fluorine groups.

3. The compound of the Formula (I) as claimed in claim 1 wherein R$^1$ is ethyl, propyl or butyl and is substituted by two to six fluorine groups.

4. The compound of the Formula (I) as claimed in claim 1 wherein R$^1$ is CF$_3$CH$_2$-, CF$_2$HCF$_2$-, CF$_3$CF$_2$-, CF$_3$CH$_2$CH$_2$-, CF$_2$HCF$_2$CH$_2$-, or CF$_3$CF$_2$CH$_2$-.

5. The compound of the Formula (I) as claimed in claim 1 selected from
5S)-5-methyl-5-[({4-[4-(2,2,2-trifluoroethoxy)phenoxy] piperidin-1-yl}sulfonyl)methyl]imidazolidine-2,4-dione;
(5S)-5-ethyl-5-[({4-[4-(2,2,2-trifluoroethoxy)phenoxy] piperidin-1-yl}sulfonyl)methyl]imidazolidine-2,4-dione;
5S-methyl-5-[({4-[4-(1,1,2,2-tetrafluoroethoxy)phenoxy] piperidin-yl}sulfonyl)methyl]imidazolidine-2,4-dione;
5S-ethyl-5-[({4-[4-(1,1,2,2-tetrafluoroethoxy)phenoxy] piperidin-yl}sulfonyl)methyl]imidazolidine-2,4-dione;
(5S)-5-methyl-5-[({4-[4-(pentafluoroethoxy)phenoxy]piperidin-1-yl}sulfonyl)methyl]imidazolidine-2,4-dione;
(5S)-5-ethyl-5-[({4-[4-(pentafluoroethoxy)phenoxy]piperidin-1-yl}sulfonyl)methyl]imidazolidine-2,4-dione;
5S-methyl-5-[({4-[3,3,3-trifluoropropoxy)phenoxy]piperidin-1-yl}sulfonyl)methyl]imidazolidine-2,4-dione;
5S-ethyl-5-[({4-[3,3,3-trifluoropropoxy)phenoxy]piperidin-1-yl}sulfonyl)methyl]imidazolidine-2,4-dione;
(5S)-5-methyl-5-[({4-[4-(2,2,3,3-tetrafluoropropoxy) phenoxy]-piperidin-1-yl}sulphonyl)methyl]imidazolidine-2,4-dione;
(5S)-5-ethyl-5-[({4-[4-(2,2,3,3-tetrafluoropropoxy)phenoxy]-piperidin-1-yl}sulphonyl)methyl]imidazolidine-2,4-dione;
(5S)-5-methyl-5-[({4-[4-(2,2,3,3,3-pentafluoropropoxy) phenoxy]-piperidin-1-yl}sulphonyl)methyl]imidazolidine-2,4-dione; and
(5S)-5-ethyl-5-[({4-[4-(2,2,3,3,3-pentafluoropropoxy) phenoxy]-piperidin-1-yl}sulphonyl)methyl]imidazolidine-2,4-dione.

6. A process for the preparation of a compound of the Formula (I) as claimed in claim 1, or a pharmaceutically-acceptable salt thereof, which comprises the reaction of a phenoxy piperidine of the Formula (II) with a sulfonyl chloride of the Formula (III)

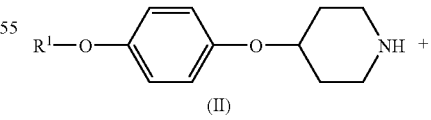

(II)

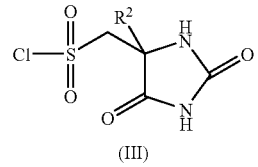

(III)

wherein R$^1$ and R$^2$ are as defined in claim 1 and wherein any functional group optionally is protected, and (i) removing any protecting groups; and (ii) optionally forming a pharmaceutically-acceptable salt.

7. A pharmaceutical composition comprising a compound of Formula (I), or a pharmaceutically acceptable salt thereof, as claimed in any one of claims 1 to 5 in association with a pharmaceutically acceptable adjuvant, diluent or carrier.

8. A method of treating rheumatoid arthritis or osteoarthritis which comprises administering to a patient a therapeutically effective amount of a compound of Formula (I) or a pharmaceutically acceptable thereof as claimed in any one of claims 1 to 5.

* * * * *